United States Patent [19]

Purdy

[11] Patent Number: 5,306,836
[45] Date of Patent: Apr. 26, 1994

[54] VOLATILE CVD PRECURSORS BASED ON COPPER ALKOXIDES AND MIXED GROUP IIA-COPPER ALKOXIDES

[75] Inventor: Andrew Purdy, Alexandria, Va.

[73] Assignee: The United States of America as represented by the Secretary of the Navy, Washington, D.C.

[21] Appl. No.: 34,802

[22] Filed: Mar. 10, 1993

Related U.S. Application Data

[62] Division of Ser. No. 828,634, Jan. 31, 1992, Pat. No. 5,213,844.

[51] Int. Cl.$^5$ .............................. C07F 1/08
[52] U.S. Cl. ...................................... 556/112
[58] Field of Search ........................... 556/112

[56] References Cited

U.S. PATENT DOCUMENTS

| | | | |
|---|---|---|---|
| 4,260,712 | 4/1981 | Aggarwal et al. | 77/428 |
| 4,681,959 | 7/1987 | Ayen et al. | 725/847 |
| 4,717,584 | 1/1988 | Aoki et al. | 826/386 |

OTHER PUBLICATIONS

Stafford et al., Can. J. Chem., 53, 1975, 817.
Loeb et al., Inorg. Chem., 18, No. 11, 1979, 3160.
Purdy et al., "New Alkoxides of Copper and the Alkaline and Alkaline-Earth Materials Crystal Structures of Na$_2$Cu [OCH(CF$_2$)$_2$]$_4$", Inorg. Chem. 30, 2812-2819 (1991).

*Primary Examiner*—José G. Dees
*Assistant Examiner*—Porfirio Nazario-Gonzalez
*Attorney, Agent, or Firm*—Thomas E. McDonnell; Barry A. Edelberg

[57] ABSTRACT

Fluorinated alkoxy compounds of copper, copper-calcium, copper-strontium, and copper-barium having the structure:

$$Cu_w(OR)_xY_yL_z, \text{ or}$$

$$M_aCu_b(OR)_c,$$

in which $1 \leq w \leq 4$; R is a fluorinated alkyl group; $x \geq 1$; Y is an alkoxy or alkyl group without beta-hydrogen; $y \geq 0$; $w \leq (x+y) \leq 2w$; L is a Lewis base; $0 \leq z \leq 2w$; M is Ca, Sr, or Ba; and $1 \leq a \leq 4$; $1 \leq b \leq 4$; $(b+2a) \leq c \leq 2(b+a)$, have exceptionally high volatilities, and hence low vaporization or sublimation temperatures, at $10^{-5}$ torr. They are superior precursor compounds for chemical vapor deposition of thin films on substrates under vacuum, and for sol-gel processing.

15 Claims, No Drawings

VOLATILE CVD PRECURSORS BASED ON COPPER ALKOXIDES AND MIXED GROUP IIA-COPPER ALKOXIDES

This is a division of co-pending application Ser. No. 07.828,634 filed on Jan. 31, 1992, now U.S. Pat. No. 5,213,844.

BACKGROUND OF THE INVENTION

1. Field of the Invention

This invention relates to novel chemical compositions for use in chemical vapor deposition. More specifically, it relates to fluorinated copper alkoxides and fluorinated calcium-copper, strontium-copper, and barium-copper alkoxides having superior physical properties for application in chemical vapor deposition to form thin films. The compounds should also be useful for the preparation of calcium, strontium, and barium-copper oxides by sol-gel processes.

Chemical vapor deposition is a process in which one or several precursor compounds and reactant gases are introduced into a reactor in the vapor phase. The reactor consists of a chamber containing the substrate upon which material is deposited from the vapor as a thin film. Most applications of chemical vapor deposition are in the manufacture of electronic components.

The precursor compound, in its original state, may be a gas, a liquid, or a solid. Gaseous precursors are directly introduced into the reactor. Liquids must be vaporized and solids sublimed to form a vapor. The transfer of vapor into the reactor, and the deposition of material from the vapor on the substrate, take place under vacuum. High deposition rates are generally desirable, and these are favored by precursor compounds having a high volatility, i.e. a high vapor pressure at a given temperature or, equivalently, having a given vapor pressure at a low temperature. A low vaporization or sublimation temperature is desirable in part because some precursor compounds thermally decompose at higher temperatures. Liquids and gases are preferred because better control is obtained over the vaporization process.

Sol-gel processes include controlled hydrolysis of the precursor in an organic solvent and heat treatment of the resulting solid product. The compounds of this invention are soluble in most organic solvents and hydrolyse easily.

2. Description of the Prior Art

Metal alkoxides are known to the art. U.S. Pat. No. 4,260,712 describes barium tertiary alkoxides used with organolithium compounds to make polymerization catalysts.

U.S. Pat. No. 4,681,959 describes the preparation of strontium, barium, gallium, indium, boron, yttrium, titanium, zirconium, and hafnium alkoxides.

U.S. Pat. No. 4,717,584 describes a method of manufacturing magnetic thin films under vacuum in a plasma using iron, barium, cobalt, and zinc alkoxides.

Fluorinated metal alkoxides are described by Abbott et al. (Inorg. Chem. 29, No. 3, 1990, 514); Stafford, Willis, Martin, and Chang (Can. J. Chem, 53, 1975, 817; ibid. 55, 1977, 2459; ibid. 55, 1977, 2465); and Loeb et al. (Inorg. Chem.18, No. 11, 1979, 3160), and Willis, C. J. (Coord. Chem. Rev., 1988, 88, 133.)

SUMMARY OF THE INVENTION

It has now been found that certain novel fluorinated copper, calcium-copper, strontium-copper, and barium-copper alkoxides have extraordinarily high volatilities and, therefore, low vaporization or sublimation temperatures, making these compounds ideal precursors for the vapor deposition of copper, calcium, strontium, and barium on substrates to form thin films. Their high solubility in most organic solvents and easy hydrolysis should also render these compounds useful for sol-gel and other hydrolysis processes. In sol-gel processing, solid metal compounds are formed by hydrolysis of organometallic precursors dissolved in organic solvents. These solid metal compounds are then heat treated.

An object of this invention is to provide novel, highly volatile, copper, calcium-copper, strontium-copper and barium-copper compounds for use in chemical vapor deposition and sol-gel processes.

DESCRIPTION OF THE PREFERRED EMBODIMENTS

The copper compounds of this invention are described by the general formula $$Cu_w(OR)_x Y_y L_z,$$

in which $1 \leq w \leq 4$; R is a fluorinated alkyl group; $x \geq 1$; Y is an alkoxy group or an alkyl group without beta-hydrogen; $y \geq 0$; $w \leq (x+y) \leq 2w$; L is a Lewis base; and $0 \leq z \leq 2w$. Typically, where Y is an alkoxy group, Y has from 1 to 7 carbons, preferably 6 carbons or less, and more preferably 4 carbons or less. Typically R and, where Y is alkyl, Y, each have from 2 to 7 carbons, preferably 2 to 6 and more preferably 4 or less carbons.

The fluorinated alkyl group is preferably selected from the group consisting of:

—CH(CF$_3$)$_2$, —CMe(CF$_3$)$_2$, —CEt(CF$_3$)$_2$,
—C(CHMe$_2$)(CF$_3$)$_2$, —C(CF$_3$)$_3$, —C(CF$_3$)$_2$CCl$_3$,
—C(CF$_2$Cl)$_3$, —C(CF$_2$Cl)$_2$CCl$_3$.

The alkoxy group is preferably selected from the group consisting of:

—O—C$_n$H$_{2n+1}$, where $1 \leq n \leq 4$.

The alkyl group without beta-hydrogen is preferably selected from the group consisting of —CH$_2$CMe$_3$ and —CH$_2$SiMe$_3$. The Lewis base is typically selected from the group consisting of:

alkyl ethers, R'—O—R', where R' is represented by C$_m$H$_{2m+1}$ and $1 \leq m \leq 4$, tetrahydrofuran (C$_4$H$_8$O, referred to herein as "THF"), and trialkyl amines, NR''R'''R'''', where R'', and R''' and R'''' are individually represented by C$_n$H$_{2n+1}$ and $1 \leq n \leq 4$, pyridine (C$_5$H$_5$N) and N,N,N',N'-tetramethyl ethylene diamine (C$_6$H$_{16}$N$_2$, referred to herein as "TMEDA". Typically, the alkyl ethers have from 2 to 7 carbons.

The calcium-copper, strontium-copper, and barium-copper halogenated alkoxides of this invention are represented by $$M_aCu_b(OR)_c.$$

where M=Ca, Sr, or Ba; $1 \leq a \leq 4$; $1 \leq b \leq 4$; $(b+2a) \leq c \leq 2(b+a)$; and R is a fluorinated alkyl group, typically C2 to C7.

The fluorinated alkyl group is preferably selected from the group consisting of:

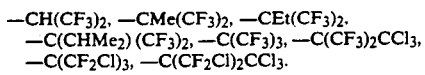

The following Table 1 summarizes the volatilization temperatures under vacuum ($10^{-5}$ torr) of some of the compounds of this invention. Table 2 summarizes data on similar compounds known to the prior art.

TABLE 1

| Compounds of This Invention | |
|---|---|
| Compound | Volatilization Temperature at $10^{-5}$ Torr |
| $Cu_4[OC(CF_3)_3]_7$ | <25° C. |
| $Cu_4[OC(CF_3)_3]_7(OEt_2)_{1-4}$ | <25° C. |
| $Cu_4[OC(CF_3)_3]_7(THF)_6$ | approx. 60° C. |
| $Cu[OC(CF_3)_3]_{0.65}(CH_2SiMe_3)_{0.35}$ | 40–70° C. |
| $BaCu_2[OCMe(CF_3)_2]_6$ | 70–90° C. |
| $Cu[OCMe(CF_3)_2]_2(TMEDA)_{0.9}$ | 60–80° C. |
| $Cu_3(\mu\text{-}OCMe_3)_4[OC(CF_3)_3]_2$ | 90–110° C. |

TABLE 2

| Prior Art Compounds | |
|---|---|
| Compound | Volatilization Temperature at $10^{-5}$ Torr |
| $[CuOCMe_3]_4$ | 100° C. |
| $Ba[(Me_3C)C(O)CHC(O)C_3F_7]_2$ | 170° C. |
| $Ba[Me_3CC(O)CHC(O)CMe_3]_2$ | 225° C. |

The preparation of the compounds of this invention is summarized by the following chemical reactions, in which R stands for a fluorinated alkoxy group:

$Ba(OR)_2 + CuCl_2 \rightarrow BaCl_2 + Cu(OR)_y$, $1 \leq y \leq 2$ $n\, Ba(OR)_2 + CuCl_2 \rightarrow BaCl_2 + Ba_{n-1}Cu(OR)_{2+2(n-1)}$ $n\, CuY_y + x\, ROH \rightarrow Cu_n(OR)_xY_{ny-x} + x\, YH$
(Y = alkyl or alkoxy)

$Cu(OR)_xY_y + z\, L \rightarrow Cu(OR)_xY_yL_z$

Specific procedures for synthesizing some of the compounds in accordance with this invention are described in Inorganic Chemistry, 1991, 30, 1969, and 1991, 30, 2812. They are included herein by reference.

Having described the invention, the following examples are given to illustrate specific applications of the invention including the best mode now known to perform the invention. These specific examples are not intended to limit the scope of the invention described in this application.

EXAMPLES

Example 1

$Cu_3(\mu\text{—}OCMe_3)_4[OC(CF_3)_3]_2$ is prepared by combining 0.23 grams of $[Cu(OCMe_3)]_2$ and 0.61 grams of $H[OC(CF_3)_3]$ in 15 ml of heptane and stirring for 18 hours. A small quantity of solids remains. After brief warming, the solvent is removed, leaving 0.25 grams of a yellow product. An NMR spectrum shows this to be approximately 75% of $Cu_3(\mu\text{-}OCMe_3)_4[OC(CF_3)_3]_2$.

Sublimation of a 129 mg portion at 110° C. affords 79 mg of $Cu_3(\mu\text{-}OCMe_3)_4[OC(CF_3)_3]_2$.

Example 2

$Cu[OC(CF_3)_3]_{0.65}(CH_2SiMe_3)_{0.35}$ is prepared by adding a solution in diethyl ether of $Me_3SiCH_2MgCl$ (7.25 mg-mol) to a mixture of CuI (7.25 mg-mol) and 20 ml of diethyl ether in an H-tube at $-23°$ C. and stirring for 15 minutes at $-23°$ C. and for 15 minutes at room temperature. The ether is removed under vacuum and pentane is added, the batch is stirred for 10 minutes and filtered to the other side of the H-tube. Filtrate is frozen with liquid nitrogen and $H[OC(CF_3)_3]$ (8.9 mg-mols) is condensed in. The mixture is warmed to room temperature and stirred for 16 hours. The solvents are removed under vacuum at 0° C. and the remaining solid is sublimed twice at 40–70° C., protected from light, affording 1.11 grams of product. Analysis shows the approximate composition to be $Cu[OC(CF_3)_3]_{0.65}(CH_2SiMe_3)_{0.35}$.

Many modifications and variations of the present invention are possible in light of the above teachings. It is therefore to be understood that, within the scope of the appended claims, the invention may be practiced otherwise than as specifically described.

What is claimed is:

1. A compound having the formula $Cu_w(OR)_xY_yL_z$, in which $1 \leq w \leq 4$; R is a fluorinated alkyl group; $x \leq 1$; Y is selected from the group consisting of alkoxy groups and alkyl groups without beta-hydrogen; $y \geq 0$; $w \leq (x+y) \leq 2w$; L is a Lewis base; and $0 \leq z \leq 2w$.

2. The compound of claim 1, wherein Y has up to 7 carbons.

3. The compound of claim 2, wherein Y is an alkyl group and R and Y have from 2 to 7 carbons.

4. The compound of claim 2, wherein Y is an alkoxy group. and R has from 2 to 7 carbons.

5. The compound of claim 1, wherein R has from 2 to 6 carbons and where Y has up to 6 carbons.

6. The compound of claim 5, wherein R has from 2 to 4 carbons and Y has up to 4 carbons.

7. The compound of claim 6, wherein each of R and Y have less than 4 carbons.

8. A compound in accordance with claim 1 in which the fluorinated alkyl group is selected from the group consisting of

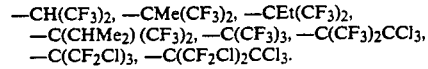

9. A compound in accordance with claim 1 in which the alkoxy group is selected from the group consisting of $-O-C_nH_{2n+1}$, where $1 \leq n \leq 4$.

10. A compound in accordance with claim 1 in which the alkyl group without beta-hydrogen is selected from the group consisting of $-CH_2CMe_3$ and $-CH_2SiMe_3$.

11. A compound in accordance with claim 1 in which the Lewis base is selected from the group consisting of alkyl ethers having the formula $R'-O-R'$, where R' is represented by $C_mH_{2m+1}$ and $1 \leq m \leq 4$; tetrahydrofuran; trialkyl amines having the formula $NR''R'''R''''$, where R'', and R''' and R'''' are individually represented by $C_nH_{2n+1}$ and $1 \leq n \leq 4$; pyridine; and N,N,N',N'-tetramethyl ethylene diamine.

12. The compound of claim 11, wherein R'—O—R' has a total of 2 to 4 carbons.

13. A compound of the formula:

$$M_aCu_b(OR)_c,$$

where M+Ca, Sr, or Ba; $1 \leq a \leq 4$; $1 \leq b \leq 4$; $(b+2a) \leq c \leq 2(b+a)$; and R is a fluorinated alkyl group.

14. The compound of claim 13, wherein R has from 2 to 7 carbons.

15. A compound in accordance with claim 13 in which the fluorinated alkyl group is selected from the group consisting of —CH(CF$_3$)$_2$, —CMe(CF$_3$)$_2$, —CEt(CF$_3$)$_2$, —C(CHMe$_2$)(CF$_3$)$_2$, —(CF$_3$)$_3$, —C(CF$_3$)$_2$CCl$_3$, —C(CF$_2$Cl)$_3$, and —C(CF$_2$Cl)$_2$CCl$_3$.

* * * * *